US00PP10780P

United States Patent [19]

Ackerman et al.

[11] Patent Number: Plant 10,780

[45] Date of Patent: Feb. 9, 1999

[54] STRAWBERRY PLANT NAMED 'PS-1150'

[75] Inventors: Stephen M. Ackerman, Salinas; Michael D. Nelson; Steven D. Nelson, both of Watsonville, all of Calif.

[73] Assignees: Plant Sciences, Inc.; Berry R & D, Inc., both of Watsonville, Calif.

[21] Appl. No.: 871,775

[22] Filed: Jun. 9, 1997

[51] Int. Cl.[6] ..... A01H 5/00

[52] U.S. Cl. ..... Plt./48

[58] Field of Search ..... Plt./48, 49

*Primary Examiner*—James R. Feyrer

*Attorney, Agent, or Firm*—Foley & Lardner

[57] ABSTRACT

This invention relates to a new and distinct winter planted short-day-type variety of strawberry known as 'PS-1150'. This new variety is primarily adapted to the growing conditions of the central coast of California with the ability to remain in fruit production from April through November. It is particularly characterized by its medium-small sized, smooth, uniformly shaped fruit. The fruit is very attractive, highly glossy, with excellent shipping qualities. The plant is strong and moderately vigorous with fruit and flowers visible above the canopy of the plant much of the year.

3 Drawing Sheets

BACKGROUND OF THE INVENTION

The present invention relates to a new and distinct short-day-type strawberry variety designated as 'PS-1150'. This new variety is a result of a cross of 'PSI-118', now referred to as 'PS-118' (U.S. Plant Pat. No. 8,205) and 'PSI-308' (U.S. Plant Pat. No. 8,346). The variety is botanically known as *F.×ananassa* Duch.

SUMMARY OF THE INVENTION

The new variety of strawberry designated 'PS-1150' resulted from a breeding program jointly sponsored by Plant Sciences, Inc. and Berry R & D, Inc., both of Watsonville, Calif., having the objective of developing new and distinct strawberry varieties. The seedling resulting from the aforementioned cross was asexually propagated by stolons in a nursery located in Lassen County, Calif., and was subsequently selected from a controlled breeding plot in Watsonville, Calif. in 1992. After its selection, the new variety was further asexually propagated in Lassen County, Calif. by stolons and extensively tested over the next several years in fruiting fields in Watsonville and Salinas, Calif. Propagation and reproduction trials have demonstrated that the combination of traits disclosed herein as characterizing the new variety are fixed and remain true to type through successive generations of asexual reproduction.

BRIEF DESCRIPTION OF THE PHOTOGRAPHS AND FIGURES

The accompanying color photographs show typical specimens of the new variety at various stages of development. The colors in the photographs are as true as it is possible to make in color reproductions. Phenotypic expressions may vary with differences in growth, environmental and cultural conditions without any change in the genotype of the variety.

Sheet 1 shows typical plant growth, flowering and fruiting characteristics in mid-July 1996. The photograph illustrates the plant vigor, visibility of the flowers above the canopy of the plant, and upright growth habit.

Sheet 2 shows a close-up of maturing fruit in mid-July 1996.

Finally, Sheet 3 shows a close-up view of fruit harvested in mid-August 1996 and packed in a standard twelve dry pint crate.

DETAILED BOTANICAL DESCRIPTION OF THE NEW VARIETY

'PS-1150' is primarily adapted to the climate and growing conditions of the central coast of California. This region provides the necessary winter temperatures required for it to produce a strong vigorous plant and to remain in fruit production from April through November. The nearby Pacific ocean provides the needed humidity and cool temperatures to maintain fruit quality during the summer production months.

'PS-1150' is a moderately vigorous plant, growing much slower in the winter and spring months as compared to 'PS-592'. When provided with optimum chilling in nursery propagation fields prior to being dug and artificial cold storage prior to being planted, the plant of the new variety is smaller and less vigorous than 'PS-592' claimed in the U.S. Plant Pat. No. 9,903 and similar to 'PS-118'. 'PS-1150' generally produces fewer runners per plant in the fruiting fields than 'PS-118'. The leaves of 'PS-1150' are smaller than both, more rounded in shape than 'PS-592' and lighter in color than 'PS-118'. 'PS-1150' has more serrations per leaf than both 'PS-118' and 'PS-592'. These serrations are also shallower than both. Petioles and petiolules are shorter in length than both 'PS-118' and 'PS-592' with the petioles smaller in diameter than 'PS-592'. Table 5 illustrates foliage characteristics of 'PS-1150', 'PS-118' and 'PS-592'.

'PS-1150' is capable of long season fruit production with fruit of acceptable size and excellent quality during the entire season when provided with optimum chilling in nursery propagation fields and artificial cold storage prior to being planted. Fruit production begins as early as mid-April in Salinas, Calif., and may continue cropping into November if rains and cold temperatures do not prevent the harvest. April production is later and lighter than 'PS-592' and similar to 'PS-118'. 'PS-1150' season average fruit size is smaller than both 'PS-118' and 'PS-592' with total seasonal yields similar to 'PS-118' and less than 'PS-592' (see Table 1).

The skin firmness and fruit gloss of 'PS-1150' is superior to 'PS-592' with better overall appearance than both 'PS-118' and 'PS-592'. See Table 3 for fruit quality performance ratings. 'PS-1150' does not tend to produce seedy tips at the apex of the fruit as compared to 'PS-118', which produces seedy tipped fruit during much of the year. The fruit surface of 'PS-1150' is smooth, with the seeds held even with the surface in contrast to 'PS-118' which tends to have a seedy surface with its seeds positioned more exerted from the surface. The fruit color of 'PS-1150' is noticeably lighter than 'PS-118' yet slightly darker than 'PS-592'. The fruit of 'PS-1150' is less conical in shape than 'PS-592' and more so than 'PS-118'. Flavor panels have rated both 'PS-118' and 'PS-592' as having better flavor than 'PS-1150' (see Table 4). The total inflorescence length of 'PS-1150' is typically shorter than both 'PS-118' and 'PS-592'. The primary peduncle during June is shorter in length than 'PS-118' and thinner in diameter than 'PS-592'. The primary pedicel is smaller in diameter than 'PS-592'. Flowers are noticeably more visible above the canopy as compared to 'PS-592'. 'PS-1150' has an anthocyanin coloration present on the upper exposed surface of all pedicels which both 'PS-118' and 'PS-592' lack. See Table 6 for inflorescence characteristics.

SPECIFIC DESCRIPTION OF THE NEW VARIETY

The following is a detailed description of 'PS-1150', including the variety's morphological, electrophoretic, past and disease reaction characteristics. This detailed description is based on observations taken during June 1996 in Salinas, Calif. Some characteristics were rated at different times, if so, the date of the evaluation will be listed. These measurements and ratings were made from plants dug from a high-elevation nursery located in Lassen County, Calif. in October 1995 and planted in Salinas, Calif. in November 1995. The characteristics of the new variety may vary in detail, depending upon variations in environmental factors, including weather (temperature, humidity and light intensity), day length, soil type and location without any change in genotype. 'PS-1150' has not been observed under all possible environmental conditions. Color terminology follows the Munsell Book of Colors, Munsell Color, Baltimore, Md. (1976).

Fruit Characteristics

'PS-1150' fruit, fruit production and runner production (fruiting field) characteristics are compred to those of 'PS-118' and 'PS-592'.

TABLE 1

1996 market fruit yield, fruit size and runner production characteristics from plants harvested from April through November of 1996 of "PS-1150" plants from a high elevation nursery (McArthur, California) dug October 15, 1995 and planted November 21, 1995 and compared with standard cultivars in Salinas, California.

| CULTIVAR | APRIL YIELD GM/PL | TOTAL YIELD GM/PL | AVERAGE FRUIT SIZE G/FR | AVERAGE RUNNERS/PL |
|---|---|---|---|---|
| 'PS-1150' | 62 | 1197 | 19.7 | 0.2 |
| 'PS-118'* | 76 | 1240 | 23.1 | 0.9 |
| 'PS-592'** | 175 | 2208 | 25.2 | 0.0 |

*'PS-118' dug October 17, 1995 and planted November 21, 1995 from McArthur, California.
**'PS-592' dug October 15, 1995 and planted November 21, 1995 from McArthur, California.

TABLE 2

Comparison of primary fruit characteristics of 'PS-1150', 'PS-118' and 'PS-592' from Salinas, California, June 19, 1996.

| CHARACTER | 'PS-1150' | 'PS-118' | 'PS-592' |
|---|---|---|---|
| Munsell Color | 7.5 R 4/10 to 7.5 R 3/8 | 7.5 R 3/10 to 7.5 R 2/8 | 7.5 R 3/12 to 7.5 R 4/12 |
| Fruit Length mean (cm) | 4.6 | 4.2 | 5.6 |
| Fruit Width mean (cm)* | 4.0 | 4.3 | 4.4 |
| Calyx Diameter mean (cm) | 5.4 | 5.4 | 5.9 |
| Sepals/Berry mean | 15.0 | 15.2 | 13.9 |
| % Soluble Solids** | 7.7 | 7.7 | 8.1 |

*Width is measured across the widest part of the berry, typically across the shoulders.
**Results are an average of 6 evaluations from fruit harvested from Salinas, California after being held for 5–6 days in cold storage.

TABLE 3

Comparison of 1995–1996 fruit quality characteristics of 'PS-1150', 'PS-118' and 'PS-592' from Salinas, California.*

| CHARACTER | 'PS-1150' | 'PS-118' | 'PS-592' |
|---|---|---|---|
| Skin Firmness | 8.4 | 8.2 | 7.5 |
| Fruit Appearance | 8.5 | 7.6 | 8.2 |
| Fruit Gloss | 8.3 | 8.5 | 7.9 |

*Results are averaged from 2 years of replicated holding tests performed from April through October 1995 and 1996. Ratings are based on a scale from 1–10; the higher the rating, the stronger the skin and the more attractive and glossy the berry.

TABLE 4

Comparison of 1996 flavor test summary of 'PS-1150, 'PS-118' and 'PS-592'*.

| CHARACTER | 'PS-1150' | 'PS-118' | 'PS-592' |
|---|---|---|---|
| Rating | 2.6 | 2.9 | 3.0 |

*Results are an average of 7 flavor tests from fruit harvested from Salinas, California after being held for 5–6 days in cold storage. Ratings are based on scores of 1–5, 5 being the best.

The fruit is medium-small in size, characteristically conic in shape and very attractive. Primary berries are typically longer than wide with only a slight tendency to develop longitudinal creases and irregular shapes. The secondary and tertiary berries are also typically longer than wide and mostly symmetrically conic in shape. The fruit also has a tendency to become slightly flat and heart shaped. The fruit surface is medium red in color with a very light colored flesh to white at the core. See Table 2 for fruit comparison characteristics. The fruit surface is smooth with the seeds held flush to the surface. The seeds are yellow and only darken slightly with prolonged exposure to direct sunlight. The seeds are spaced evenly over the surface of the berry with seedy tipped fruit rare. The flesh is very firm and glossy with good texture and acceptable flavor. See Tables 3 and 4, respectively, for fruit quality and flavor characteristics. The calyx of the primary berry is medium in diameter with overlapping sepals. The calyx attaches slightly below the base of the fruit with necked fruit uncommon. The sepals are narrow elliptical to ovate in shape with acute apexes. Primary berry sepals are serrated with secondaries and tertiaries only occasionally serrated. Fruit skin is considered only slightly susceptible to cracking due to rain. Pollination is rarely adversely affected by rain.

Plant Characteristics

The plant of 'PS-1150' is medium in size with multiple crowns producing very few runners if given the proper chilling levels prior to being dug, and artificially, prior to being planted. Excessive chilling will result in an over-vigorous plant with a reduction in total fruit yield and increased runner production. Although the plant may become over-vigorous and slightly dense if provided with excessive field chilling and/or artificial cold storage prior to being planted, it generally does not become too large unless chilling and/or storage levels greatly exceed acceptable limits. The plants grow very slow during the winter and spring months after planting, but by early summer they have reached good vigor. The foliage grows upright on short thin petioles. The plant canopy has a relatively medium-light colored appearance.

Foliage Characteristics

'PS-1150' foliage chracteristics are compared to those of 'PS-118' and 'PS-592'.

TABLE 5

Comparison of leaf characteristics of 'PS-1150', 'PS-118' and 'PS-592' from Salinas, California, June 19, 1995.

| CHARACTER | 'PS-1150' | 'PS-118' | 'PS-592' |
|---|---|---|---|
| Munsell leaf color (upper Surface) | 7.5 GY 3/4 to 7.5 GY 4/4 | 7.5 GY 3/4 | 7.5 GY 4/4 |
| Terminal leaflet Length mean (cm) | 9.0 | 9.5 | 11.2 |
| Terminal leaflet Width mean (cm) | 7.9 | 8.9 | 8.9 |
| Terminal leaflet ratio (L/W) | 1.14 | 1.06 | 1.26 |
| Petiole length mean (cm) | 17.8 | 22.5 | 20.9 |
| Petiole width mean (mm) | 4.0 | 4.0 | 5.0 |
| Petiolule length mean (mm) | 7.3 | 13.5 | 10.3 |
| Serrations/leaf | 20.3 | 18.2 | 18.6 |
| Serration depth mean (mm) | 4.8 | 6.2 | 6.2 |

The foliage of 'PS-1150' is relatively small to medium in size, non-glossy, medium-light in color and lightly rugose with a tendency to cup upward at the margins. The terminal leaflet is longer than wide as described by the length/width ratio. See Table 5 for foliage comparision characteristics. Leaflets have a moderate number of relatively small and shallow serrations at the margins, with moderately acute apexes. These serrations typically occur singly, very seldom in doubles. Petioles are considered medium in length and thin in diameter with bract leaflets commonly occurring singly or in pairs. Petiolules are also considered short. Pubescence on the petioles grow irregularly perpendicular to the petiole and irregularly parallel to the upper and lower leaf surface.

Flowers and Inflorescences

'PS-1150' inflorescence characteristics are compared to those of 'PS-118' and 'PS-592'.

TABLE 6

Comparison of inflorescence characteristics of 'PS-1150', 'PS-118' and 'PS-592' from Salinas, California, June 19, 1996.

| CHARACTER | 'PS-1150' | 'PS-118' | 'PS-592' |
|---|---|---|---|
| Inflorescence Length mean (cm) | 28.2 | 32.2 | 32.9 |
| Primary Peduncle Length mean (cm) | 15.8 | 18.8 | 15.2 |

TABLE 6-continued

Comparison of inflorescence characteristics of 'PS-1150', 'PS-118' and 'PS-592' from Salinas, California, June 19, 1996.

| CHARACTER | 'PS-1150' | 'PS-118' | 'PS-592' |
|---|---|---|---|
| Primary Peduncle Width mean (mm) | 4.3 | 4.3 | 5.8 |
| Primary Pedicel Length mean (cm) | 6.0 | 5.6 | 6.6 |
| Primary Pedicel Width mean (mm) | 2.7 | 2.5 | 3.4 |

The inflorescences of 'PS-1150' are medium in length, extending the flowers and fruit beyond the foliage during much of the season. The inflorescence remains erect and visible above the canopy of the plant much of the year until the weight of the ripening fruit causes them to fall to the sides of the bed. The primary peduncle is considered short and thin especially at the time of the evaluation. The pedicel holding the primary berry is considered medium in length and thickness, and, may originate singly from the apex of the primary peduncle or only occasionally from one of the secondary peduncles. Secondary and tertiary berries are borne on pedicels arising from secondary peduncle apexes. Anthocyanin coloration (color near 5R 4/8) is present on the exposed surfaces of primary pedicels and secondary and tertiary pedicels and peduncles. See Table 6 for inflorescence comparison characteristics. Flowers are medium in size and readily visible above the canopy of the plant. Anthers produce an abundance of pollen for good pollination, even during adverse weather conditions when pollination of other varieties may be compromised. Flowers produce an average of 5 to 7 obovate shaped petals per flower. Typically a bract leaf is borne on a short petiole which originated at the primary peduncle apex alongside the base of one of the secondary peduncles. Bract leaves may also occur at the apex of secondary peduncles. Pubescence occurs on all peduncles and pedicels, growing irregularly perpendicular to all surfaces.

Isozymes in Leaf Extract

'PS-1150' isozyme banding characteristics are compared to those of 'PS-118' and 'PS-592'.

TABLE 7

'PS-1150' isozyme banding characteristics are compared to those of 'PS-118' and 'PS-592'.

| CULTIVAR | PGI | PGM |
|---|---|---|
| 'PS-1150' | A7 | C2 |
| 'PSI-118' | A7 | C4 |
| 'PS-592' | A8 | C2 |

Studies of protein polymorphism in strawberry by the starch gel electrophoresis method were conducted at Plant Sciences, Inc. to characterize this newly developed variety and distinguish it from similar appearing varieties. See Table 7 for the isozyme banding patterns of 'PS- 1150', compared to 'PS-118' and 'PS-592'.

Isozymes were extracted from young leaves and characterized, using starch gel electrophoresis techniques. The following isozymes were charaterized: phosphoglucoisomerase (PGI: EC 5.3.1.9) and phosphoglucomutase (PGM: EC 2.7.5.1).

The testing used both field and greenhouse grown plant material, all grown in Watsonville, Calif. Newly mature leaves (0.5 g fresh weight) from the growing crowns were used. Samples were collected in the morning, held at 4C and analyzed within six hours.

The tissue preparation, extraction and staining are as reported in S. Arulsekar and D. E. Parfitt, "Isozyme Analysis Procedures for Stone Fruits, Almond, Grape, Walnut, Pistachio, and Fig", HortScience 21(4): 928-933.

Following electrophoresis, the gel was sliced and stained for each enzyme system. Banding patterns were interpreted as they developed, and gel slices were fixed in 50% glycerol. The banding pattern codes shown in Table 7 are those of Bringhurst et al. (1981).

In addition, a series of precise molecular markers have been determined for this new variety for unique identification.

Pest Reactions

The new variety may not be resistant to any of the known insects, diseases or viruses common in California. It is known to be moderately susceptible to grey fruit mold, angular leafspot and only slightly susceptible to powdery mildew. The susceptibility of the new variety to any of the virus complexes of California has not been determined.

We claim:

1. A new and distinct strawberry variety designated 'PS-1150', as herein described and illustrated.

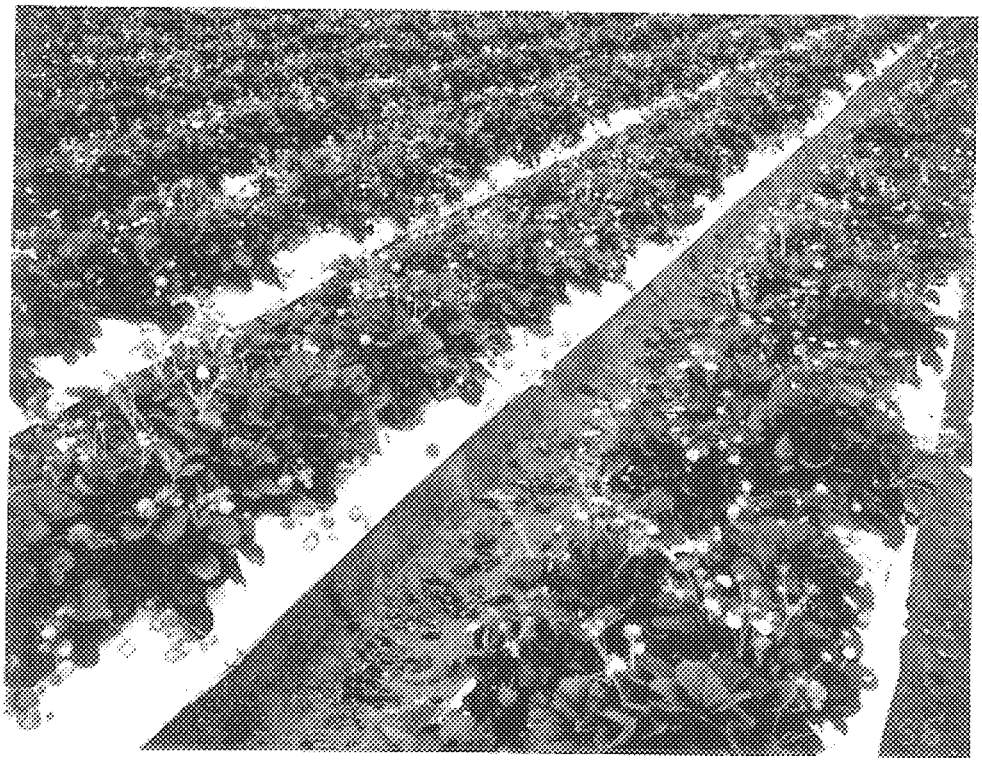

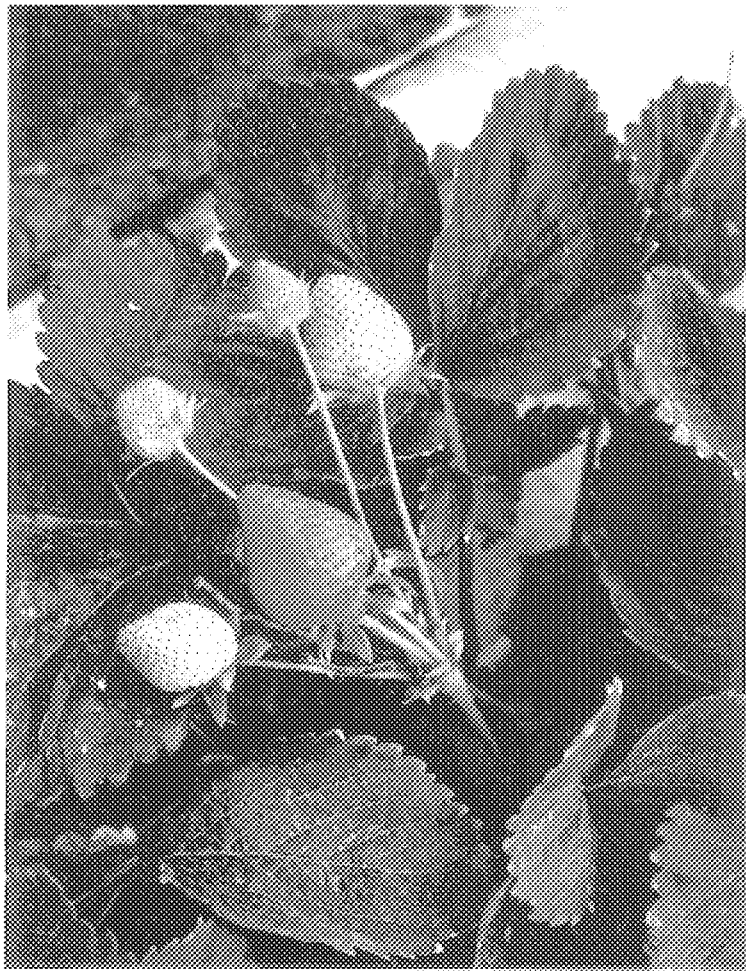

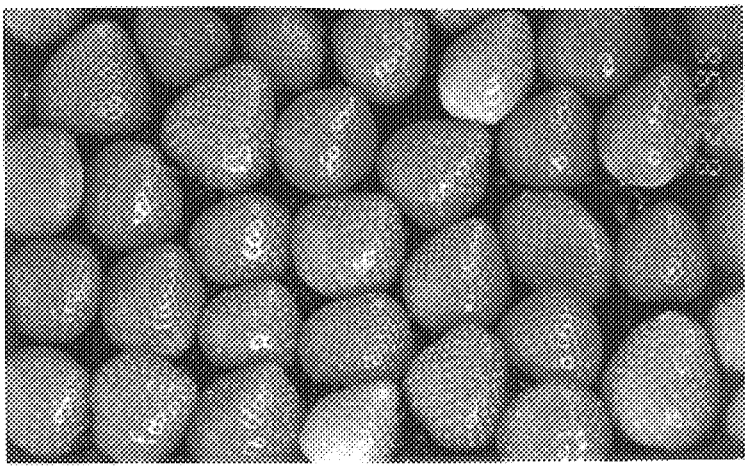
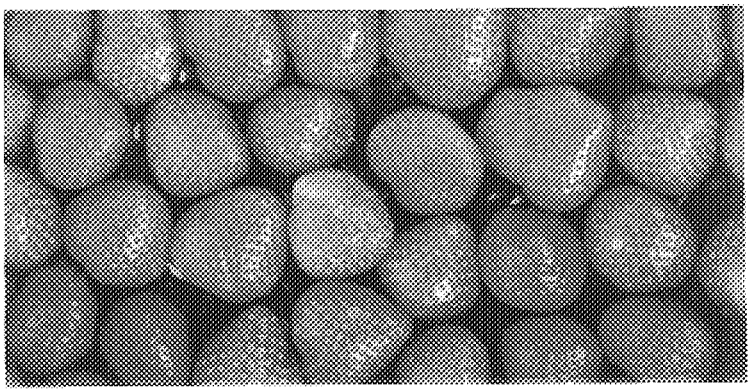

* * * * *